United States Patent [19]

Lübbers et al.

[11] Patent Number: 5,376,336
[45] Date of Patent: Dec. 27, 1994

[54] APPARATUS FOR DETERMINING THE FLOW OF MATTER PASSING THROUGH A BOUNDARY SURFACE

[75] Inventors: Dietrich W. Lübbers, Dortmund, Germany; Hellfried Karpe, Graz, Austria

[73] Assignee: Medical Instruments AG, Schaffhausen, Switzerland

[21] Appl. No.: 878,294

[22] Filed: May 6, 1992

[30] Foreign Application Priority Data

May 10, 1991 [AT] Austria ............... A 976/91

[51] Int. Cl.⁵ ............... G01N 21/27; C12M 1/34; C12M 1/40; A61B 5/00
[52] U.S. Cl. ............... 422/82.06; 128/633; 250/281; 422/82.07; 422/86; 435/288; 435/291; 435/808
[58] Field of Search ............... 435/288, 291, 300, 808, 435/807, 817; 422/82.03, 82.05, 82.07, 82.08, 86, 91; 436/62, 68, 127, 136, 172; 128/632, 633, 637, 664, 665; 250/281, 458.1

[56] References Cited

U.S. PATENT DOCUMENTS

| 4,005,700 | 2/1977 | Parker ............... 128/632 |
| 4,073,713 | 2/1978 | Newman ............... 204/403 |
| 4,306,877 | 12/1981 | Lubbers ............... 436/166 |
| 4,401,122 | 8/1983 | Clark ............... 128/635 |
| 4,580,059 | 4/1986 | Wolfbeis et al. ............... 250/459.1 |
| 4,632,807 | 12/1986 | Marsoner ............... 422/82.08 |
| 4,657,736 | 4/1987 | Marsoner et al. ............... 422/56 |
| 4,752,115 | 6/1988 | Murray et al. ............... 385/12 |
| 4,775,514 | 10/1988 | Barnikol et al. ............... 422/82.08 |
| 4,877,747 | 10/1989 | Stewart ............... 436/525 |
| 4,892,640 | 1/1990 | Wolfbeis et al. ............... 204/418 |
| 5,030,420 | 7/1991 | Bacon et al. ............... 422/87.07 |
| 5,034,330 | 7/1991 | Yamori et al. ............... 435/288 |
| 5,069,214 | 12/1991 | Samaras et al. ............... 128/633 |
| 5,081,041 | 1/1992 | Yafuso et al. ............... 436/68 |
| 5,157,262 | 10/1992 | Marsoner et al. ............... 250/458.1 |
| 5,173,434 | 12/1992 | Morris et al. ............... 436/172 |

Primary Examiner—Robert J. Warden
Assistant Examiner—Robert Carpenter
Attorney, Agent, or Firm—Watson, Cole, Grindle & Watson

[57] ABSTRACT

An apparatus for determining the flow of matter passing through a boundary surface, which is provided with at least one sensing layer corresponding to the boundary surface, and presents a known or predetermined, finite resistance to the material flow, and wherein an optical indicator is provided in the sensing layer for obtaining a first measured value of a quantity dependent on the mean concentration of matter in the sensing layer, and wherein a second measured value of this quantity is known on one side of the sensing layer, or can be determined by means of another optical indicator provided in a second sensing layer, and, further, wherein an evaluation unit is provided for inferring the material flow from the difference of the two values measured.

43 Claims, 3 Drawing Sheets

APPARATUS FOR DETERMINING THE FLOW OF MATTER PASSING THROUGH A BOUNDARY SURFACE

BACKGROUND OF THE INVENTION

The invention relates to an apparatus for determining tile flow of matter passing through a boundary surface.

Flow of matter or material flux in this context denotes a flow of particles, for instance, ions, molecules or gases, which passes through an interface or boundary between different media, or different phases of one medium, and whose intensity per unit of area and time is to be quantified, for example, in particles per second and square meter, or $mol\ s^{-1}\ m^{-2}$.

If it is possible to determine particle concentration, partial gas pressure, etc., on both sides of an interface, the corresponding material flow may be inferred from the difference of the measured values. Problems arise if the necessary data cannot be obtained on one side of the interface, or if they are not accurate enough.

SUMMARY OF THE INVENTION

It is an object of the invention to propose an apparatus which will permit measurement of the material flow even if one side of the interface is inaccessible or barely accessible for measuring purposes, in particular, if the Interface is constituted by the surface of an organ or the skin.

In the invention this object is achieved by providing the interface with at least one corresponding sensing layer which presents a known or predetermined, finite resistance to the material flow, and by providing the sensing layer with an optical indicator in order to obtain the first measured value of a quantity dependent on a mean concentration of matter in the sensing layer, and by providing that a second measured value of this quantity be known on one side of the sensing layer, or be determined by means of another optical indicator provided in a second sensing layer, and, further, by providing an evaluation unit for inferring the material flow from the difference of the two measured values. When using the apparatus of the invention, all concentration measurements are taken on one side of the interface, which will help master the problems referred to hereinbefore. The principle of measurement is explained in detail in the description of the drawings, using four basic variants of the invention (FIGS. 1 to 4). In the layers corresponding to the interface the particles or molecules to be measured should neither be generated nor destroyed (e.g., by chemical reaction) nor attached, in order to obtain an unbiased result.

Unless the sensing layer is used as a resisting layer at the same time, it may be proposed in further development of the invention that at least one resisting layer be provided, which should be adjacent to the sensing layer or located between the two sensing layers, and which should present a known or predetermined, finite resistance to the material flow. In this instance the sensing layer may be configured as a very thin layer with practically no resistance to the material flow, and its indicator (for example, a luminescence-optical indicator) may be directly immobilized on the resisting layer.

Suitable materials for the resisting layer include hydrogel, latex, controlled pore glass (CPG), cellophane, or a nucleopore membrane. The sensing layer may be made of PVC, polyurethane, silicone, hydrogel, latex, or cellulose, for instance.

Possible indicators for determination of the $O_2$ flow are, for example, pyrene butyric acid, decacyclene, and ruthenium and osmium complexes (bipyridile, phenanthroline). For determination of the flow of $H^+$ ions or the flow of $CO_2$ hydroxypyrene trisulphonic acid may be used.

For the determination of gas flow it may be provided according to the invention that all sensing and resisting layers be permeable at least to the gas being measured, at least one of the optical indicators being suitable for determining a quantity dependent on partial gas pressure or gas concentration.

In a particularly advantageous variant used for determination of the flow of one or more gases such as $O_2$, $CO_2$, $H_2$, $NH_3$, water vapor, or anaesthetic gases, passing through an interface represented by the surface of an organ, for instance, the skin, a frame is provided, which is open on both sides, one side being placed on the surface of the organ, and which holds the gas-permeable sensing and resisting layers, one side of the sensing layer for determining the partial gas pressure being adjacent to the surface of the organ, while the other side is connected to a reservoir containing a gas of known composition, a resisting layer being provided between the sensing layer and the reservoir, if necessary. For determination of the $O_2$ flux or $CO_2$ flux through the skin, only one sensing layer is required, as the $O_2$ or $CO_2$ content of the air may, for many applications, be assumed to be sufficiently constant to enter into the evaluation directly as a constant.

In context of flow measurement of organs, such as the human skin, it will be an advantage if the frame can be covered with a gas-tight cap on the side of the frame facing away from the surface of the organ. After the frame has been covered, the oxygen stored in tile sensing layer and, if present, in the resisting layer, is absorbed through the skin, thus reducing the $O_2$ partial pressure at the surface of the skin. From the rate of pressure change the supply of blood in the observed skin area may be inferred.

It will be an advantage in this context if the sensing layer or layers and, possibly, a resisting layer are arranged in a thermostat-control led frame, or rather, if at least one of the sensing and/or resisting layers is made of electrically conductive polymer material, which is provided with electrical contacts, in order to permit resistance heating. The amount of current drawn for resistance heating may also be used for assessing the blood supply of the skin area under observation.

The invention will also permit the use of a gas supply unit as a gas reservoir, possibly thermostat-controlled, which may be attached to the frame. In this way a $pCO_2$ or $pO_2$ differing from the gas content in the air may be applied to the side of the polymer layer facing away from the surface of the skin. For example, pure oxygen may be offered, or an inert gas, or a gas influencing the exchange processes at the skin surface, and in this way the corresponding gas flow may be determined as a function of the partial gas pressure applied from outside, thereby supplying further parameters on the gas kinetics of the skin.

Temperature control, or rather, control of the resistance heating, is best effected by additionally providing at least one of the sensing layers with an optical indicator for temperature measurement. It is obvious that the thermometric or heating units described here are not restricted to measuring the gas flow at the surface of an organ or the skin, but are all suitable for other applications as well, as will be discussed below.

The basic idea of the invention may be exploited for a variety of purposes. For determining ionic flow, for instance, all sensing and/or resisting layers may he ion-permeable, the optical indicator present in at least one of the sensing layers being suitable for determination of a quantity dependent on ionic concentration. Such a device, for example, will permit monitoring of the ionic exchange between a nutrient solution and a donor organ stored therein, thereby supplying information on the condition of the organ without necessitating the taking of samples. In a preferred variant the sensing layer and, if present, the resisting layer has a ionic carrier for measuring an ion from the group of $Na^+$, $K^+$, $Li^+$, $Mg^{2+}$, $Ca^{2+}$, $Cl^-$, $NH_4^+$.

Ionic concentration may be determined according to a method described in U.S. Pat. No. 4,892,640. In this instance a PVC membrane is provided with a ionic carrier and a charged fluorogen, which is forced out of the membrane if a charged species (electrolyte) is introduced, in order to maintain the electric neutrality of the membrane. As a consequence, very high fluorogen concentrations are encountered at the sensor boundary, which will cause fluorescence quenching due to a concentration affect.

In an enhanced variant of the invention for determining the flow of a gas participating in a biochemical reaction (by being consumed or generated), a reaction chamber may be provided which contains a biochemical substrate, preferably an enzyme, and is in contact with the sensing layer and, at least indirectly, with a sample containing an agent to be determined, preferably a corresponding enzyme reactant, the concentration of the agent in the sample being determined as a variable depending on the gas flow value obtained from the evaluation unit.

In a variant of the invention with a sample chamber configured as a flow cell the proposal is put forward that at least one further sensing layer and, if necessary, a further resisting layer, be provided between the reaction chamber and a sample chamber, the sensing layer and the resisting layer being permeable both to the gas participating in the biochemical reaction and to the corresponding agent in the sample.

The reaction chamber may contain a cell culture, for example, whose reaction to a toxic substance contained in the sample is measured via the gas metabolism of the cell culture.

In a further variant of the invention the reaction chamber may contain the enzyme glucose oxidase (GOD) for determining the glucose concentration, or the enzyme lactic dehydrogenase or lactic oxygenase for determining the lactate concentration in a sample, the, or rather, each sensing layer being provided with an indicator for determining the $pO_2$ value. Other examples applying this principle of measurement are as follows;

| enzyme | enzyme reactant |
|---|---|
| xanthine oxidase | hypoxanthine |
| alcohol oxidase | ethanol |
| lactic monooxygenase | lactate |
| glycerol dehydrogenase | glycerol |

The biochemical substrate, or rather, the enzyme, is preferably provided in a layer which is immobilized on the side of the sensing layer facing the reaction chamber.

To increase the measuring sensitivity of the apparatus, or prevent substances interfering with the measuring process from entering the immobilized layer, the layer containing the biochemical substrate may be provided with a membrane on the side facing the reaction chamber having the desired selective permeability.

A further application is provided by proposing that for the purpose of determining the flow of an enzyme reactant, all sensing and/or resisting layers be permeable to the enzyme reactants participating in an enzymatic reaction, where the sensing layer or layers used for measuring the concentration of one of the enzyme reactants contains an enzyme from the group of oxidases and oxygenases and the appropriate flavine coenzyme (FMN, FAD), whose intrinsic fluorescence depends on the concentration of the enzyme reactant. With the use of this variant of the apparatus of the invention the flow of glucose between a nutrient solution and the culture feeding on it may be monitored, if the interface between nutrient solution and culture is provided with an apparatus as described above.

Although all known sensing layers may be used with the apparatus of the invention as long as they are permeable to the particles or molecules to be measured, and all principles of optical measurement, such as absorption measurement, reflection measurement, etc., are permissible, it will be an advantage for the sensing layer (optode) to contain a luminescence-optical indicator.

It is further required, especially in applications where the apparatus of the invention is located at the end of a fiber-optical waveguide, that the sensing layer and the resisting layer be transparent to the exciting radiation and/or the radiation emitted by the indicator.

Finally, it will be an advantage, in particular for all instances in which the sensing layer must be permeable to enzyme reactants, if the optical indicator is placed in nanocapsules which are evenly distributed within the sensing layer.

In material flow measurements it is often necessary to find the site (or sites) within a larger area where the flow of a substance, such as oxygen, is disturbed. For this purpose the spatial, i.e., topographical distribution of flow should be determined. This is of particular importance in applications involving skin tests, for instance, as a suitable $O_2$ flux sensor would permit detection of all sites where microcirculation disturbances develop.

To achieve this aim, the proposal is put forward that a measuring device coupled to the evaluation unit be provided which should scan the area of the sensing layer or layers to detect the topographical distribution of the material flow. Topographical resolution of the device depends on the diffusion characteristics of its sensing layers, as topographical differences of concentrations (pressures) may lead to cross-diffusion within the sensing layer, which will degrade topographical resolution.

According to the invention this can be prevented by adjusting the diffusion characteristics of the sensing layer to those of the object to be measured. In order to obtain the highest possible topographical resolution, the diffusion coefficients of the sensing layers should be significantly smaller than those of the object to be measured.

Topographical resolution can be further improved by embedding the sensing layer in a mesh of metal, glass, or special plastic materials with high diffusion coefficients, preventing cross-diffusion in the sensing layer. Topographical resolution will be defined by the mesh width.

In a special variant the mesh may consist of metal wire or optical fibers, for instance, and may be used for temperature-control of the flux sensor. The optical fibers may also be used as part of the optical measuring configuration, e.g., to introduce the excitation light into the sensing layer.

In medical applications, for instance, it is often required that several parameters be measured simultaneously, in order to arrive at a more reliable diagnosis. It will be better, for instance, to monitor not only the local flow and pressure of oxygen in a particular area, but also—with the use of auxiliary units—the haemoglobine $O_2$ saturation (with the use of an oximeter) and the behavior of the erythrocite flow rate (using the laser Doppler method) in the same area. For this purpose the sensing and resisting layers should be configured so as to be transparent to the wavelengths of the auxiliary optical elements. The indicators should be selected so as not to interfere with the optical analysis in the auxiliary equipment. As the different measurement variables can be characterized by different optical signals (e.g., different spectral emission or absorption), they can be analyzed separately by means of a multi-component analysis even if they are registered simultaneously.

BRIEF DESCRIPTION OF THE DRAWINGS

Following is a more detailed description of the invention as illustrated by the attached drawings, in which.

DETAILED DESCRIPTION OF THE PREFERRED EMBODIMENTS

Figure 1:
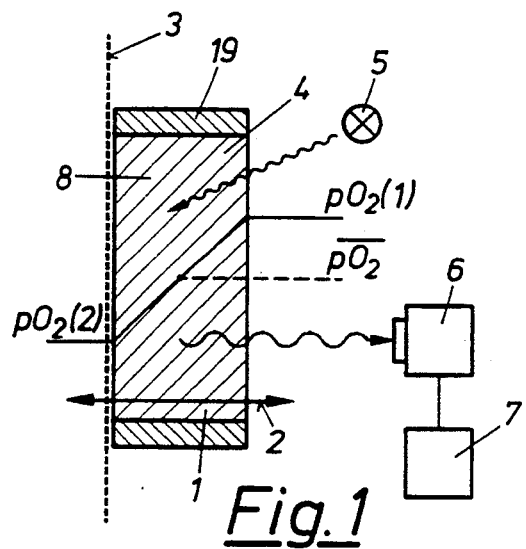
FIG. 1 presents an apparatus of the invention for determining the material flow through an interface.

The apparatus presented in FIG. 1 has a sensing layer 4, which presents a known or predetermined, but finite resistance to the material flow passing through the interface 3 indicated by arrow 2. The sensing layer 4 is provided with an optical indicator 8 used for measuring the concentration of the matter (e.g., oxygen) whose flow is to be determined. For this purpose the indicator 8 must change at least one of its optical properties, depending on the material concentration. Excitation of the optical indicator 8 is effected via a light source 5; between the light source 5 and the detector 6 filter elements may be provided, which are not shown here. The light emitted by the sensing layer 4, or rather, the indicator 8, is passed to a detector 6, which is connected with an evaluation unit 7. A suitable indicator would be a luminescence-optical indicator, for example, which is chemically or physically immobilized on the sensing layer in known spatial distribution. The sensing layer 4 may be laterally held in a frame 19.

In this simple variant the sensing layer 4 also acts as a resisting layer 1 for the material flow to be measured. Using the $O_2$ flux through the interface 3 as an example, the principle of measurement may be explained as follows:

Departing from a known partial oxygen pressure $pO_2$ (1), e.g., of the ambient air, and an unknown $pO_2$ (2) on the other side of the interface 3, a partial pressure will build up in the sensing layer, varying with the individual parameters and the thickness of the layer, whose mean pressure $\overline{pO_2}$ is measured by the detector 6.

The $O_2$ flux $J(O_2)$ is defined by $$J(O_2) = P_1(pO_2(1) - pO_2(2)) = P_2(pO_2(1) - \overline{pO_2}) \tag{1}$$

with $$P_1 = \alpha . D/d$$

and $$P_2 = K_1 . P_1$$

$\alpha$ ... solubility coefficient
$D$ ... diffusion coefficient
$d$ ... thickness of layer
$K_1$ ... indicator distribution coefficient If the concentration of the respective matter on one side of the sensing layer 4 is known, the simplest version of the invention does not require more than one sensing layer to determine the material flow $J(O_2)$ from the difference between a measured value $(\overline{pO_2})$ and a constant $(pO_2(1))$.

In the instance of variations in the concentration of matter on the two sides of the interface 3, a second sensing layer 9 is provided parallel to the first sensing layer 4, its indicator 8' differing from the first indicator 8. This variant is presented in FIG. 2. The sensing layers may, but need not, consist of different materials. The $O_2$ flow, for example, is then determined as follows:

$$J(O_2) = P_3(\overline{pO_2}(1) - \overline{pO_2}(2)) \tag{2}$$

$P_3$ is a constant, which depends on the parameters of layers 4 and 9, and on the distribution coefficients of the indicators 8, 8' as well as geometry factors of the configuration.

Figure 3:
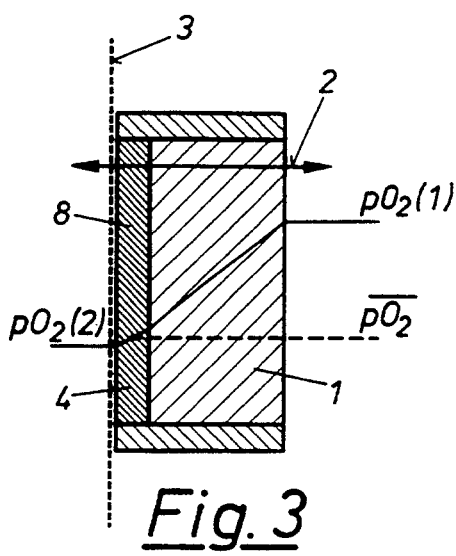
FIGS. 2 to 4 present variants of FIG. 1.
Figure 4:
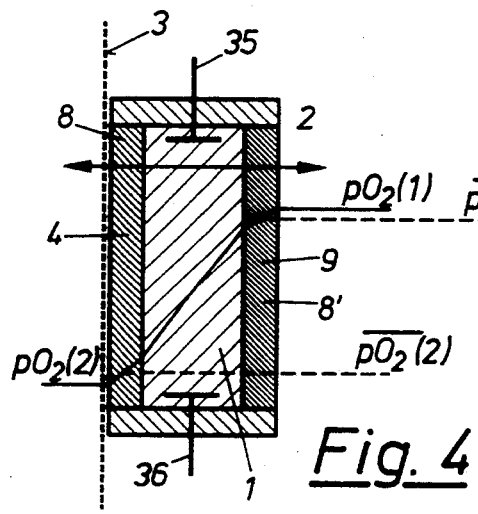
Figure 2:
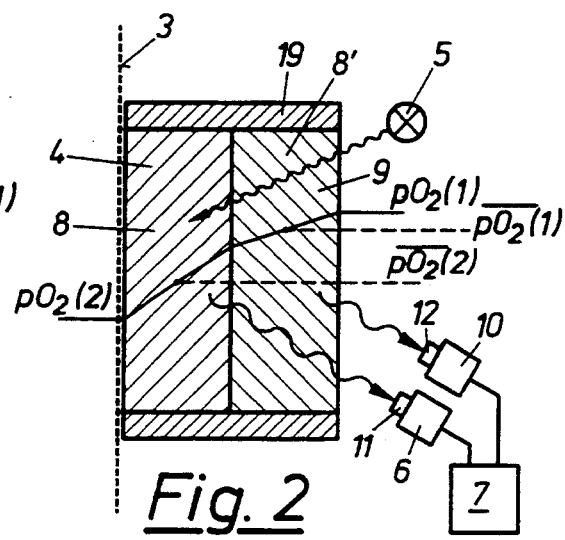

FIGS. 3 and 4 present variants of the invention corresponding to those of FIGS. 1 and 2, with a resisting layer 1 adjacent to the sensing layer 4 (FIG. 3) or 1 situated between the two sensing layers 4 and 9 (FIG. 4). Since the sensing layers 4 and 9 are only used for measuring purposes in this case, they may be kept very thin and should not present any resistance to the material flow, such that $$\overline{pO_2}(1) \sim pO_2(1)$$

and $$\overline{pO_2}(2) \sim pO_2(2)$$

As the resisting layer 1 is responsible for the formation of the material concentration gradients, its parameters $\alpha$, $D$ and the thickness $d$ must be known or determinable. In all other respects the flow is determined in accordance with equations (1) and (2), with suitably modified constants.

For temperature control one of the layers tin FIG. 4 the resisting layer 1, for instance) may be made of electrically conductive polymer material, and resistance heating may be provided via electrical contacts 35, 36.

In the configuration of FIG. 1 the sensing layer 4 must also be transparent to tile exciting radiation and the radiation emitted by the indicator 8.

The radiation paths of the sensing layers 4 and 9 towards the corresponding detectors 6 and 10 of the variant of FIG. 2 must be separated optically, unless different indicator materials 8 and 8' are used, whose radiation is separated by entrance filters 11 and 12 at the detectors 6 and 10. It will also be possible to use only one detector separating the two radiations by employing a rapidly turning filtering disk with different entrance filters.

The interface marked 3 may be transparent to the exciting radiation or the radiation emitted by the sensing layers, which will permit the use of a configuration based on transmitted light deviating from the optical configuration in FIG. 1.

The layer configurations shown in FIGS. 2 and 4 form a complete sensor for determination of the material flow (flux sensor). In the configurations in FIGS. 1 and 3 the concentration of matter on one side of the interface 3 must be known. Depending on external conditions, one of the flux sensors of FIGS. 1 to 4 may be used with the variants of FIGS. 5 to 10 discussed below.

Figure 5:
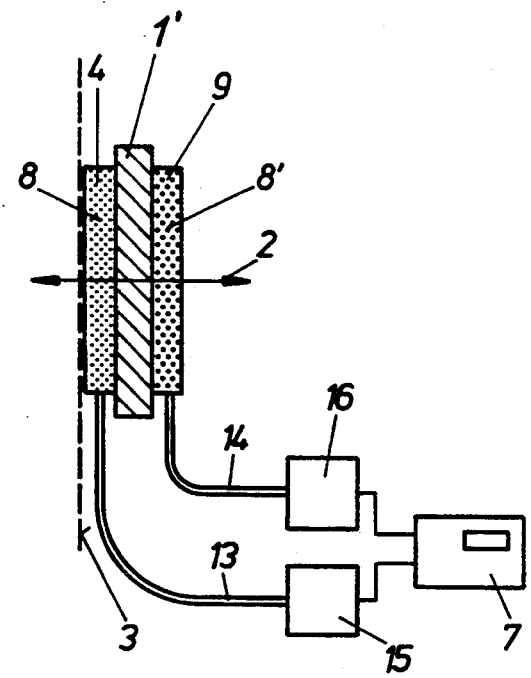
FIG. 5 presents a variant of FIG. 4.

In the variant of FIG. 5 the sensing layers (optodes) 4 and/or 9, and the indicators 8, 8' are excited by optical fibres 13 and 14 entering laterally. Inside the sensing layers the light is guided by total reflection, for instance. The preferably two-armed optical fibres 13 and 14 each are connected to excitation and measuring units 15 and 16, which in turn are connected to the evaluation unit 7. In this variant the resisting layer 1' may be opaque (e.g., a blackened hydrogel), and may also be used for optical separation of the two measuring radiations, in which case both optodes may contain the same indicator 8.

Figure 6:
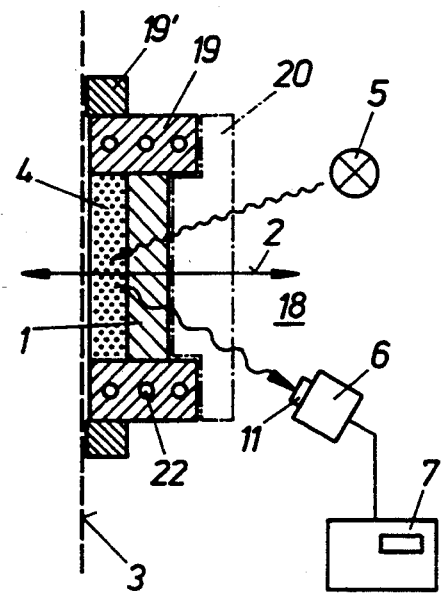
FIG. 6 presents a variant for determining the gas exchange through the surface of the skin.

FIG. 6 presents a variant which may be used, e.g., for measuring the $O_2$ flow through the skin representing the interface 3 in this case. Since the $O_2$ partial pressure in the ambient air here serving as a gas reservoir 18 is known, or can be determined with the use of variables such as atmospheric pressure, humidity and temperature, only one $O_2$ optode or sensing layer 4 is required, which together with the resisting layer 1 is held laterally in a frame 19 open on both sides. The frame 19 may be controlled by a thermostat, as indicated by the reference number 22. In a configuration to be discussed in greater detail in the description of FIG. 7, a gas-tight cap 20 may be put on the frame 19 in order to inhibit the flow of gas. The frame 19 has a fastening element 19' permitting its attachment to the skin, for example, by applying an adhesive or a vacuum.

Figure 7:
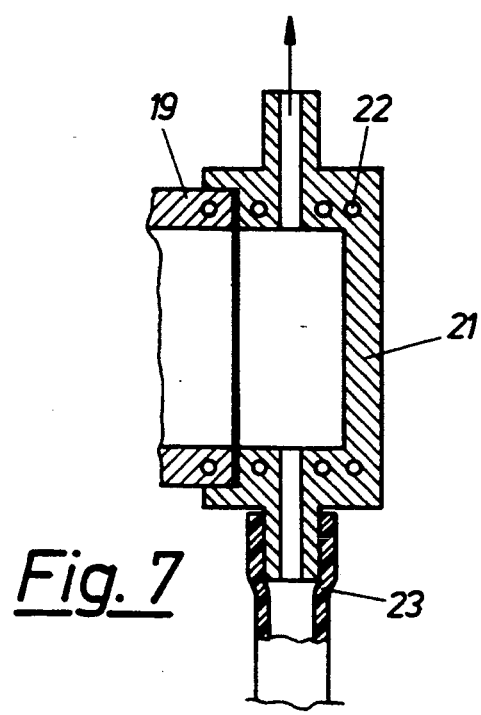
FIG. 7 presents an auxiliary unit for the variant of FIG. 6.

FIG. 7 shows a thermostat-controlled gas supply unit 21 which may be attached to the frame 19 instead of the cap 20. The gas supply unit 21 is connected to a gas source (not shown in this drawing) via a feeder line 23. The apparatus presented in FIGS. 6 and 7 will permit noninvasive measurement of the transcutaneous oxygen partial pressure of the skin, for example.

Figure 8:
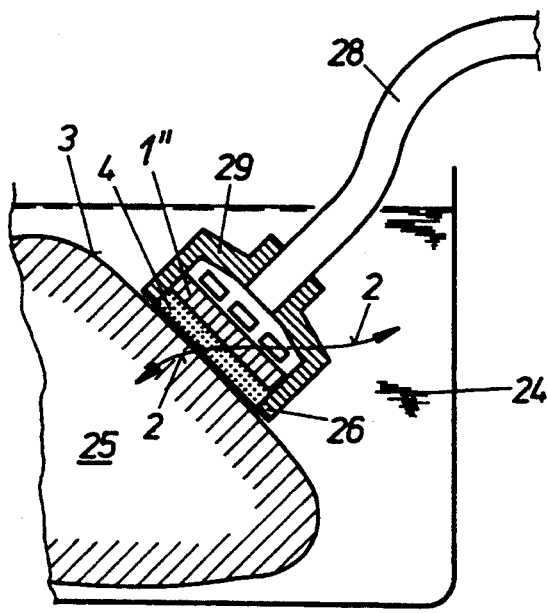
FIG. 8 presents a variant for monitoring ionic flux.

A possible variant of the invention is presented in FIG. 8, where the apparatus is used for ionic flux monitoring. In this instance the ionic flux can be determined between a nutrient solution 24 and a donor organ 25 stored therein, by placing a frame 26 onto the surface of the organ 3 (=interface), which includes an ion-permeable, transparent resisting layer 1" (e.g., a hydrogel layer) and an ion-permeable sensing layer 4 (e.g., blackened hydrogel layers) located between the resisting layer 1" and the surface of the organ. The frame 26 further holds an optical fiber 28 directed towards the sensing layer 4, which will transmit the exciting and the measuring radiation. In order to maintain the ionic flux (e.g., sodium, potassium, calcium, chloride ions, etc.) in the direction of arrows 2, a chamber is provided above the resisting layer 1" into which the nutrient solution 24 will flow through orifices 29. If the volume of the nutrient solution is large enough, the ionic concentration of the solution may be considered almost constant, and thus one sensing layer 4 will be required only. This sensing layer could serve as a resisting layer at the same time (cf. FIG. 1). In all other applications a configuration as in FIG. 2 or 4 may be selected, comprising two sensing layers 4 and 9, and permitting also opaque, ion-permeable resisting layers 1" (e.g., blackened hydrogel layers).

Suitable sensing and/or resisting layers for electrolytic measurement are above all PVC layers with ionic carriers. They permit measurement of ions such as $Na^+$, $K^+$, $Li^+$, $Mg^{2+}$, $Ca^{2+}$, $Cl^-$, $NH_4^+$.

For this purpose PVC is used, for instance, in which a chromo-ionogenic substance and two ionic carriers are dissolved. One ionic carrier will transport the $H^+$ ion, the other ionic carrier is specific to the analyte under test ($Na^+$, $K^+$, ...). The $H^+$-specific ionic carrier will transport $H^+$ ions between the sample, or the resisting layer, and the chromo-ionogenic substance, i. e., a pH indicator whose spectral characteristics will vary with the $H^+$ concentration. From solutions with a constant pH and different electrolyte concentrations, the $H^+$ ion is transported towards the chromo-ionogenic substance, or away from it, only if the electric charge of the membrane is changed by the transport of the analyte ($Na^+$, $K^+$, ...). This sensor principle is based on the transport of analyte and $H^+$ ion, maintenance of electron neutrality, and the presence of a constant pH value in the sample; it will work only if these requirements are met.

Figure 9:
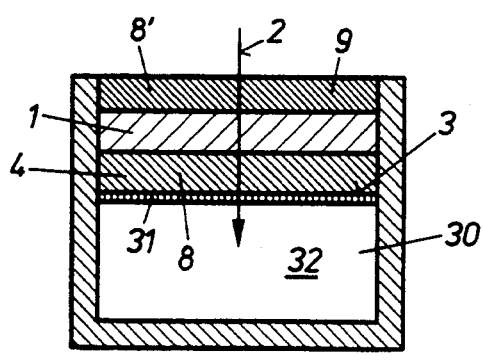
FIGS. 9 and 10 present a variant for measuring the concentration of an enzyme reactant.

With a variant as presented in FIG. 9 the concentration of an agent, for instance, an enzyme reactant, may be determined in a sample 32. The apparatus includes a reaction chamber 30 containing a biochemical substrate, e.g., an enzyme, which may be immobilized on the sensing layer 4, for example. If the enzyme reactant of a sample 32 introduced into the reaction chamber 30, reacts with the enzyme or the enzyme layer 31—a gas required for the enzymatic reaction (e.g., $O_2$) streaming into the reaction chamber 30 along arrow 2—, the concentration of the enzyme reactant may be inferred from the gas flow. If the partial gas pressure on the side facing away from the reaction chamber 30 is constant,, there will be no need for the sensing layer 9.

Figure 10:
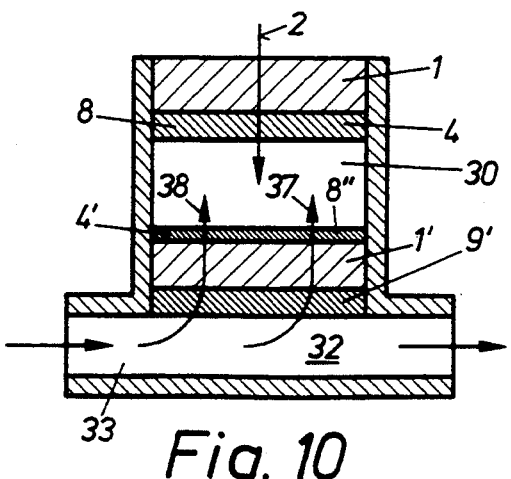

If the gas required for the enzymatic reaction, e.g., oxygen, is dissolved in the sample itself, another flux sensor comprising a resisting layer 1' and sensing layers 4' and 9', for instance, must be provided between the reaction chamber 30 and the sample chamber 33 configured as a flow cell, in order to avoid errors of measurement. Such a configuration is shown in FIG. 10. This flux sensor must be gas-permeable (arrow 37) as well as permeable to the enzyme reactant under test (arrow 38) (e.g., utilize hydrogel layers). If the gas to be monitored is homogeneously distributed in the reaction chamber 30, and if the same gas partial pressure is prevailing in the sensing layers 4 and 4', the sensing layer 4' with the indicator need not be provided.

For determination of glucose concentration, for example, the enzyme layer 31 in FIG. 9 or the reaction chamber 30 in FIG. 10 may contain the enzyme glucose oxidase (GOD), the sensing layers 4 and 9 determining the $pO_2$ values from which the $O_2$ flow may be inferred.

The configurations presented in FIGS. 1 to 4 would also be suitable for measuring the flow of an enzyme reactant, e.g. through the surface of an organ. For this purpose the sensing and resisting layers must be permeable to the enzyme reactant under test. For measuring the enzyme concentration on the two sides of a resisting layer 1, optical sensing elements 4 and 9 are provided which contain an enzyme from the group of oxidases and oxygenases and a corresponding flavine coenzyme (FMN, FAD). By measuring the intrinsic fluorescence of the coenzyme, the respective concentration of the enzyme reactant is determined in the evaluation unit, and the flow of the enzyme reactant through the interface 3 is inferred from the difference of the concentration values. With the appropriate sensing elements, an optical configuration without a resisting layer may be used, similar to the one presented in FIG. 2.

The principle of measurement and the apparatus discussed herein could also be used in applications with a known flow and a known concentration of matter on one side of an interface, in which the unknown concentration of matter on the other side is to be determined.

Furthermore, an apparatus as shown in FIG. 9 or 10 could be used for determining the $O_2$ consumption of a cell culture or a nutrient solution provided with bacteria.

To eliminate stray light, or to optically separate different light paths, the sensing layers 4, 9 and the resisting layer 1 may be pigmented or blackened. Silicone or hydrogel layers, for instance, may be blackened with carbon black or iron oxide, or they may contain colloidal particles of precious metal, such as gold or platinum, in microdisperse distribution.

Figure 11:
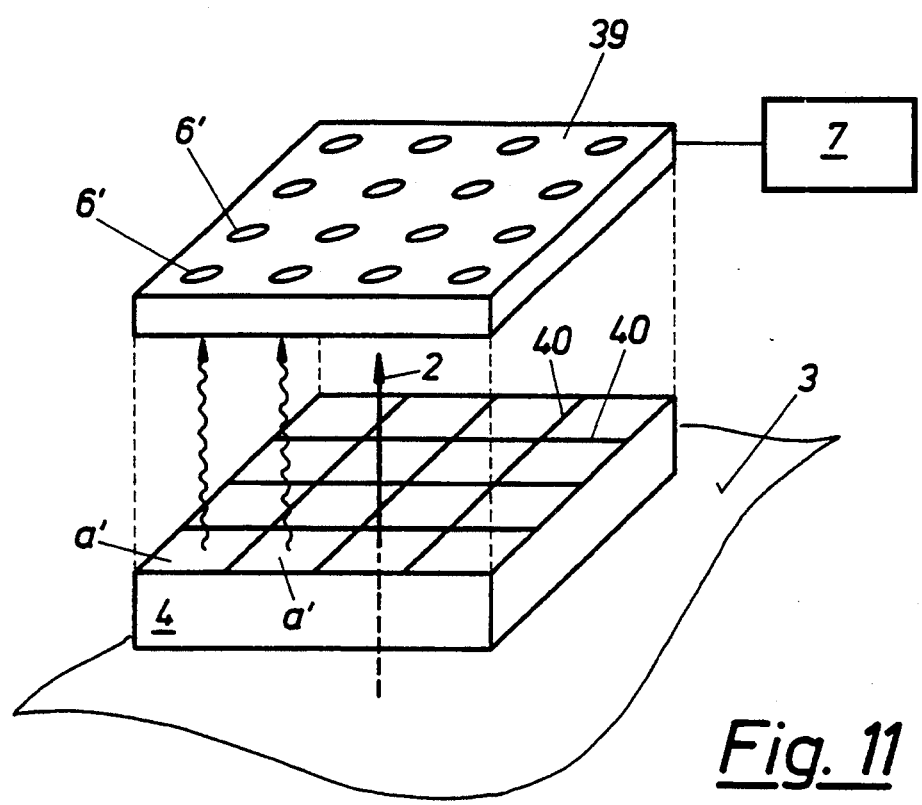
FIG. 11 presents an apparatus for measuring the topographical distribution of the material flow.

By means of the apparatus shown in FIG. 11 the topographical distribution of the material flow (e.g., $O_2$ flow) through an interface 3 (e.g., skin) may be determined. For this purpose a measuring device 39 is provided for scanning the area of the sensing layer 4. The measuring device 39 either may have a large number of detectors 6', each assigned to a corresponding area a' of the sensing layer 4, or it may be provided with only one detector scanning the areas a' sequentially. Preferably an imaging device (e.g., a CCD)) is used which is directly placed on the sensing layer 4.

To reduce cross-diffusion in the sensing layer 4, the latter may be embedded in a mesh 40 with a high diffusion coefficient. The mesh 40 may consist of optical fibers, for instance, for introducing the excitation light, or of metal wire for temperature control of the sensing Layer 4.

We claim:

1. An apparatus for determining a material flux passing through a boundary surface, comprising:
a sensor that defines opposite first and second sensor surfaces, said first sensor surface being positionable against a boundary surface, said sensor providing a known finite resistance to material flux passing therethrough from a first area adjacent said first sensor surface thereof to a second area adjacent said second surface thereof, said sensor including a first sensing layer,
a first optical indicating means in said first sensing layer for providing a first measured value of a quantity dependent on a mean concentration of said material in said first sensing layer, an excitation means for radiating excitation light towards said first sensing layer to excite said first optical indicator means therein, and
an evaluation means for determining material flux through said sensor from a comparison of said first measured value and a second value of said quantity in one of said first and second areas adjacent said boundary surface.

2. An apparatus according to claim 1, wherein said sensor means includes a resistance layer adjacent said first sensing layer, said resistance layer providing said known finite resistance to material flow.

3. An apparatus according to claim 1, wherein said sensor means includes a second optical indicating means for providing said second value.

4. An apparatus according to claim 3, wherein said sensor means includes a second sensing layer which contains said second optical indicating means.

5. An apparatus according to claim 4, wherein said sensor means includes a resistance layer sandwiched between said first and second sensing layers, said resistance layer providing said known finite resistance to material flow.

6. An apparatus according to claim 1, further comprising a detector means for detecting an optical property of light emitted by said excited optical indicator means, said detector means being electrically connected to said evaluation means.

7. An apparatus according to claim 6, further comprising an optical fiber which conveys said excitation light from said excitation means towards said first sensing layer and which conveys light emitted by said excited optical indicator means to said detector means.

8. An apparatus according to claim 1, wherein said material whose flux is determined is a gas, wherein said sensor is permeable to said gas, and wherein said first optical indicating means measures a quantity dependent on partial pressure or concentration of said gas in said first sensing layer.

9. An apparatus according to claim 1, wherein said material whose flux is determined is an ion, wherein said sensor is permeable to said ion, and wherein said first optical indicating means measures a quantity dependent on concentration of said ion in said first sensing layer.

10. An apparatus according to claim 9, wherein said ion is selected from the group consisting of $Na^+$, $K^+$, $Li^+$, $Mg^{2+}$, $Ca^{2+}$, $Cl^-$ and $NH_4^+$.

11. An apparatus according to claim 1, wherein said material whose flux is determined is an enzyme reactant, wherein said sensor is permeable to said enzyme reactant, and wherein said first optical indicating means comprises an enzyme selected from oxidases and oxygenases and a flavine coenzyme selected from FMN and FAD.

12. An apparatus according to claim 1, wherein said first optical indicating means is a luminescence optical indicator.

13. An apparatus according to claim 1, wherein said sensor includes a second optical indicating means for providing an indication of the temperature of said sensor.

14. An apparatus according to claim 1, further comprising measuring device electrically connected to said evaluation means, said measuring device scanning an area of said first sensing layer to detect a topographical distribution of material flux.

15. An apparatus according to claim 14, further comprising a mesh in which said first sensing layer is embedded, said mesh preventing cross diffusion of material in said first sensing layer.

16. An apparatus according to claim 15, wherein said mesh consists of optical fibers.

17. An apparatus according to claim 15, wherein said mesh consists of a metal wire which can be used to control the temperature of said first sensing layer.

18. An apparatus according to claim 2, wherein said material whose flux is being determined is a gas, wherein said sensor is permeable to said gas, and wherein said first optical indicating means measures a quantity dependent on partial pressure or concentration of said gas in said first sensing layer.

19. An apparatus according to claim 18, further comprising a frame which is open at opposite first and second ends and which mounts said sensor therein such that when said frame is placed on a surface of an organ constituting said boundary surface, said first sensing layer will be positioned adjacent said organ surface; and a reservoir connected to said second end of said frame, said reservoir containing a known concentration of a gas selected from the group consisting of $O_2$, $CO_2$, $H_2$, $NH_2$, water vapor and anaesthetic gas, said sensor determining the flux of said gas through said organ surface.

20. An apparatus according to claim 19, further comprising a gas-tight cap covering said second end of said frame.

21. An apparatus according to claim 19, further comprising a gas supply unit attached to said second end of said frame to supply a flow of said gas to said frame.

22. An apparatus according to claim 21, wherein said material whose flux is determined is an ion, wherein said sensor is permeable to said ion, and wherein said first optical indicating means measures a quantity dependent on a concentration of said ion in said first sensing layer.

23. An apparatus according to claim 22, wherein said ion is selected from the group consisting of $Na^+$, $K^+$, $Li^+$, $Mg^{2+}$, $Ca^{2+}$, $Cl^-$ and $NH_4^+$.

24. An apparatus according to claim 18, further comprising a reaction chamber, said sensor being positioned in communication which said reaction chamber, an enzyme positioned in contact with said first sensing layer and in communication with a sample containing an enzyme reactant, said enzyme and said enzyme reactant reacting with consumption of gas which flows into said reaction chamber through said sensor, said apparatus determining gas flux through said sensor and enabling determination of enzyme reactant concentration in said sample.

25. An apparatus according to claim 24, further comprising a sample chamber containing said sample with enzyme reactant, and including a sensor positioned between the sample chamber and the reaction chamber, said second sensor being permeable to gas and said enzyme reactant.

26. An apparatus according to claim 24, wherein said enzyme is glucose oxidase for determining concentration of glucose as the enzyme reactant in a sample, said first optical indicator indicating a $pO_2$ value.

27. An apparatus according to claim 24, wherein said enzyme is immobilized in a layer on a side of said first sensing layer facing said reaction chamber.

28. An apparatus according to claim 27, wherein said enzyme is contained in a membrane of selective permeability.

29. An apparatus according to claim 2, wherein said material whose flux is determined is an enzyme reactant, wherein said sensor means is permeable to said enzyme reactant, and wherein said first optical indicating means comprises an enzyme selected from oxidases and oxygenases and a flavine coenzyme selected from FMN and FAD.

30. An apparatus according to claim 3, wherein said first optical indicating means is immobilized as a layer on said resistance layer.

31. An apparatus according to claim 3, wherein said sensor is transparent to excitation energy used to excite said first optical indicating means and to radiation emitted thereby.

32. An apparatus according to claim 1, wherein said first optical indicator means is in capsules evenly distributed within the first sensing layer.

33. An apparatus according to claim 1, further comprises a thermostat-controlled frame in which said sensor means is positioned.

34. An apparatus according to claim 33, wherein at least one of said first sensing layer and said resistance layer is composed of an electrically-conductive polymer material, and including electrical contacts connected to said polymer material for resistance heating thereof.

35. An apparatus according to claim 3, wherein said material whose flux is determined is a gas, wherein said sensor is permeable to said gas, and wherein said first optical indicating means measures a quantity dependent on partial pressure or concentration of said gas in said first sensing layer.

36. An apparatus according to claim 3, wherein said material whose flux is determined is an ion, wherein said sensor is permeable to said ion, and wherein said first optical indicating means measures a quantity dependent on a concentration of said ion in said first sensing layer.

37. An apparatus according to claim 3, wherein said material whose flux is determined is an enzyme reactant, wherein said sensor is permeable to said enzyme reactant, and wherein said first optical indicating means comprises an enzyme selected from oxidases and oxygenases and a flavine coenzyme selected from FMN and FAD.

38. An apparatus according to claim 5, wherein said material whose flux is being determined is a gas, wherein said sensor is permeable to said gas, and wherein said first optical indicating means measures a quantity dependent on partial pressure or concentration of said gas in said first sensing layer.

39. An apparatus according to claim 5, wherein said material whose flux is determined is an ion, wherein said sensor is permeable to said ion, and wherein said first optical indicating means measures a quantity dependent on a concentration of said ion in said first sensing layer.

40. An apparatus according to claim 39, wherein said ion is selected from the group consisting of $Na^+$, $K^+$, $Li^+$, $Mg^{2+}$, $Ca^{2+}$, $Cl^-$ and $NH_4^+$.

41. An apparatus according to claim 5, wherein said material whose flux is determined is an enzyme reactant, wherein said sensor is permeable to said enzyme reactant, and wherein said first optical indicating means comprises an enzyme selected from oxidases and oxygenases and a flavine coenzyme selected from FMN and FAD.

42. An apparatus according to claim 36, wherein said ion is selected from the group consisting of Na+, K+, Li+, Mg$^{2+}$, Ca$^{2+}$, Cl− and NH$_4$+.

43. An apparatus according to claim 24, wherein said enzyme is lactic hydrogenase or lactic oxygenase, wherein said enzyme reactant in said sample is lactate, and wherein said first optional indicating means measures a pO$_2$ value.

* * * * *

UNITED STATES PATENT AND TRADEMARK OFFICE
CERTIFICATE OF CORRECTION

PATENT NO. : 5,376,336

DATED : December 27, 1994

INVENTOR(S) : Dietrich Werner Lübbers and Hellfried Karpf

It is certified that error appears in the above-indentified patent and that said Letters Patent is hereby corrected as shown below:

On the title page, Items [75] and [73] should read;

[75] Inventors: Dietrich W. Lübbers, Dortmund, Germany; Hellfried Karpf, Graz, Austria

[73] Assignee: AVL Medical Instruments AG, Schaffhausen, Switzerland

Signed and Sealed this

Twenty-first Day of March, 1995

Attest:

BRUCE LEHMAN

*Attesting Officer*     *Commissioner of Patents and Trademarks*